United States Patent
Risser

(10) Patent No.: US 9,128,068 B1
(45) Date of Patent: Sep. 8, 2015

(54) SAMPLE CONDITIONING SYSTEMS AND METHODS

(71) Applicant: Scott Risser, Tucson, AZ (US)

(72) Inventor: Scott Risser, Tucson, AZ (US)

( * ) Notice: Subject to any disclaimer, the term of this patent is extended or adjusted under 35 U.S.C. 154(b) by 0 days.

(21) Appl. No.: 14/301,163

(22) Filed: Jun. 10, 2014

(51) Int. Cl.
*B01D 53/64* (2006.01)
*G01N 33/00* (2006.01)

(52) U.S. Cl.
CPC ........ *G01N 33/0045* (2013.01); *G01N 33/0013* (2013.01); *B01D 53/64* (2013.01); *B01D 2257/602* (2013.01)

(58) Field of Classification Search
CPC .. B01D 50/00; B01D 53/64; B01D 2257/602; G01N 7/08; G01N 21/00
USPC ..................................... 436/181; 422/83, 168
See application file for complete search history.

(56) References Cited

U.S. PATENT DOCUMENTS

| | | | |
|---|---|---|---|
| 3,884,639 A * | 5/1975 | Sugiyama | 436/81 |
| 7,454,952 B2 | 11/2008 | Kita et al. | |
| 7,736,602 B1 | 6/2010 | Kita et al. | |
| 7,928,033 B2 | 4/2011 | Akiyama et al. | |
| 2006/0243096 A1 | 11/2006 | Kita et al. | |
| 2007/0092418 A1* | 4/2007 | Mauldin et al. | 423/210 |
| 2007/0092419 A1* | 4/2007 | Fan et al. | 423/210 |
| 2008/0188002 A1 | 8/2008 | Kato et al. | |
| 2009/0130013 A1 | 5/2009 | Higgins | |

OTHER PUBLICATIONS

J. Wang, Z. Xiao and O. Lindqvist, "On-Line Measurement of Mercury in Simulated Flue Gas" Water, Air, and Soil Pollution, 80, 1217-1226, 1995.*
Shelley, Crystalline Marble Beats Limestone for Fluegas Desulfurization, NovaCon Energy Systems, Inc., Bedford, N.Y., Environmental Engineering World, May-Jun. 1996, p. 20.

* cited by examiner

*Primary Examiner* — Christopher A Hixson
*Assistant Examiner* — Emily Berkeley
(74) *Attorney, Agent, or Firm* — Quarles & Brady LLP; Gavin J. Milczarek-Desai

(57) ABSTRACT

Sample conditioning systems and methods especially useful for converting non-elemental forms of mercury to elemental form. The systems involve a reactor having a heater, with the reactor configured such that a heated sample is flowed through a calcareous sorbent during heating and then cooled in the presence of a solid metal that is more chemically active or less noble than mercury. The methods may be used as a part of an emissions monitoring process to insure compliance with emission standards and to precisely gage the amount of abatement needed.

7 Claims, 5 Drawing Sheets

Reactor Packing Configuration

SAMPLE CONDITIONING SYSTEMS AND METHODS

BACKGROUND OF THE INVENTION

1. Field of the Invention

This disclosure relates to the monitoring and processing of emissions and waste streams, and more particularly, to monitoring and processing emissions and waste streams containing mercury.

2. Description of the Related Art

Recent environmental awareness has focused on the need to remove harmful mercury emissions from the emissions of systems such as coal fired power plants. These efforts have led to several developments with regards to effective mercury removal techniques. Nonetheless, knowing precisely how much sorbent or other mercury treatment must be utilized so as to better control costs and other aspects of mercury abatement has remained elusive.

All current mercury-monitoring technologies only respond to elemental mercury (as opposed to ionic forms or organic compounds of mercury). Thus, monitoring mercury found in the environment from natural or human-caused sources requires a conversion system and method to convert all forms of mercury present to elemental mercury. Standardized conversion methods are all wet chemical methods currently utilized or approved by various agencies.

However, as an in between method, sorbent traps are the most common method currently implemented for mercury emission determination. Sorbent traps capture mercury from a sample stream from an emission source for a preset amount of time. The trap is then removed and the mercury driven off in one of several methods, captured and analyzed per the procedure for the wet methods mentioned above and the mercury emission rate calculated based on the time in service and sample flow rate. The broad use of sorbent traps is an indication that the mercury Continuous Emissions Monitoring (CEM) technology still is not considered adequate for monitoring.

In typical streams containing mercury, both elemental and ionic forms of the metal exist. The ionic mercury is present as a halogenated mercuric compound (e.g. chloride) and/or mercury oxide. Organic mercury such as methyl mercury also may be present on other processes involving organic wastes from fish processing or the breakdown of organics around mercury containing soils.

In the standard wet chemistry method of converting ionic and/or organic forms of mercury into elemental form, all mercury is trapped and ultimately reduced in a solution to elemental form. This solution is then stripped and sent to an analyzer of one of many methods to determine the elemental mercury concentration of the solution. From this, calculations are performed based on the amount of gasses or other source material to determine the actual mercury concentration in the source. This method is a complicated and lengthy batch process, subject to errors.

Thus, there is a need for a rapid, continuous, dry conversion process that provides reliable, high accuracy results in all common environments from all forms of mercury. This process would allow for better control of conversion chemicals, sorbent, and/or other mercury abatement chemicals.

SUMMARY OF THE INVENTION

Embodiments described herein relate to systems and methods for "conditioning" waste stream and/or emission samples that contain mercury, whereby conditioning includes any conversion or abatement chemistry as well as methods involving the processing and/or monitoring of mercury. The systems and methods detailed herein are based on a multi-point conversion approach involving the thermal reduction/smelting of mercury to its elemental form, stable calcareous acid gas removal, and a galvanically reducing environment for cool down of the now elemental mercury.

In some embodiments, a heated sample is additionally contacted with a catalytic surface material that is integrated with the calcareous sorbent or that is disposed between the calcareous sorbent and the solid metal that is more chemically active or less noble than mercury. The catalytic surface material may include quartz and/or alumina.

Further embodiments described herein include a continuous plug flow packed reactor. The reactor is made of materials capable of operation of at least 1100° C. The reactor is fitted with fans on both the inlet and outlet of the reactor to blow air across the tube to eliminate heat conduction down the length of the reactor to subsequent fittings. Heat is further dissipated with radiation barriers that also function as cooling fins on the reactor wall.

In some embodiments, the flow of mercury laden gases that are drawn into the reactor are heated inside a bed of catalytic surface material, such as marble chips and quartz chips integrated together. These perform two functions: 1) the marble chips remove acid gas components from the gas stream to drive the equilibrium reaction toward elemental mercury and 2) the quartz chips provide active sites for the mercury to adsorb onto for decomposition. By combining marble and quartz chips, etching of the quartz by acid gases is minimized. In other words, having more active sites on the quartz allows for a lower residence time for the reaction and more thorough reaction and conversion. The flow exits the reactor and is diverted to the outer walls for faster quench cooling. The quenching along with a galvanic substance such as iron maintains the mercury in elemental form, i.e., the mercury will not oxidize during cooling.

Additional features and advantages of the invention will be forthcoming from the following detailed description of certain preferred embodiments when read in conjunction with the accompanying drawings.

DESCRIPTION OF THE PREFERRED EMBODIMENTS

Figure 1:
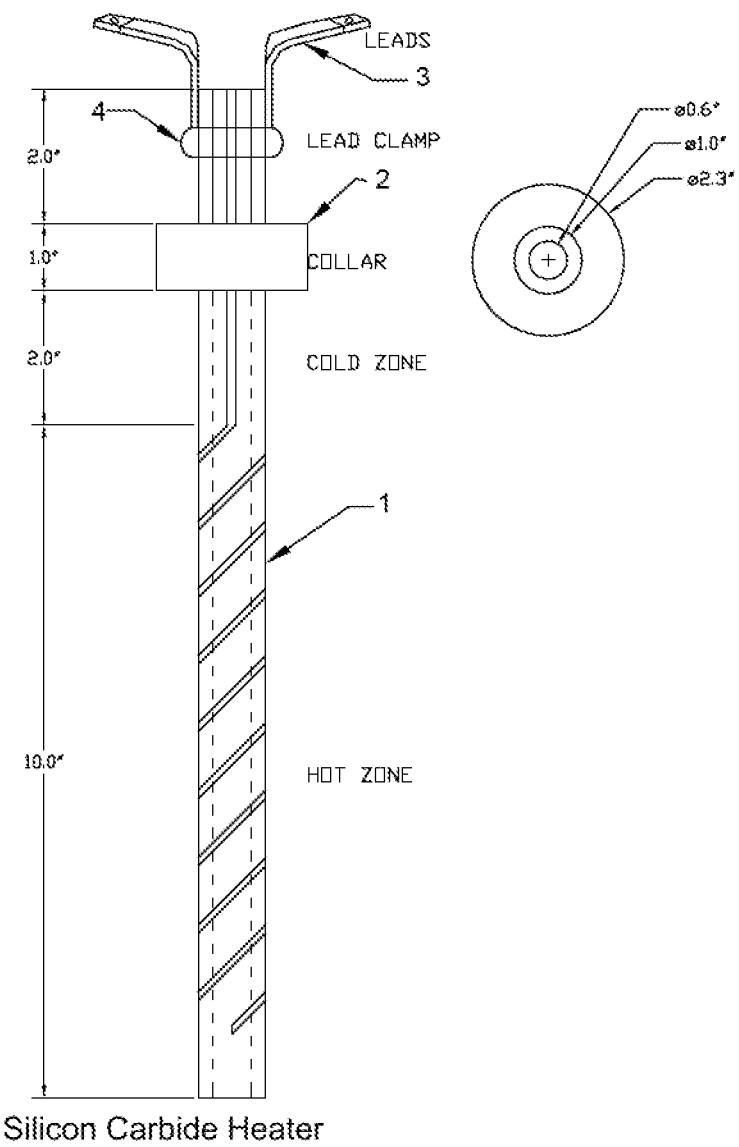
FIG. 1 schematically illustrates a silicon carbide heater (prior art).

FIG. 1 shows a typical silicon carbide heating element 1 used to heat the reactor. The element is made from a machined silicon carbide. The heating element is fitted with a mounting collar 2 and metal braid leads 3 to attach to a power source and a lead clamp 4, which holds the leads to the heating element.

Figure 2:
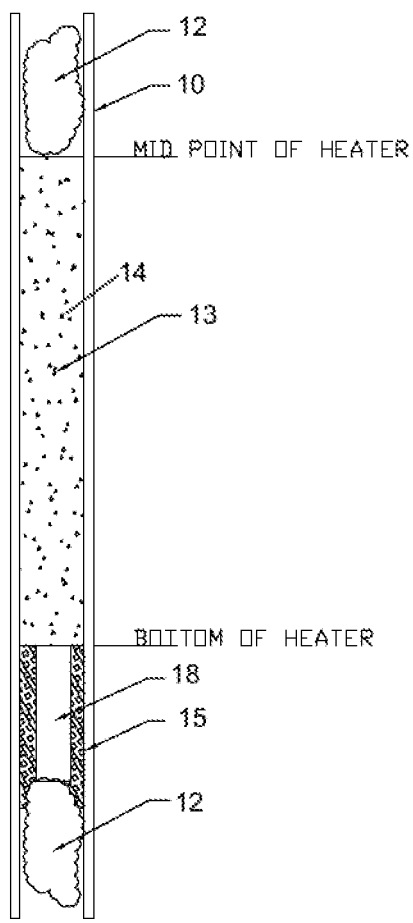
FIG. 2 depicts a reactor packing configuration according to an embodiment of the invention.

FIG. 2 illustrates a typical reactor packing material arrangement as modified according to an embodiment of the invention. The reactor is made from an alumina tube 10. The inlet end of the reactor contains a small spun alumina ceramic insulation plug 12 to hold materials in place. At approximately the midpoint of the heater length down the reactor as shown in the figure, a sorbent zone containing marble chips 13 of approximately 1/8" to 1/4" grade are added along with similar sized quartz chips 14, the quartz creating a catalytic surface material zone. Near the end of the heater element, baffling material 18 is present, and, inserted around the baffling material 18, steel shot 15 is added and the bottom is plugged with another plug of ceramic insulation 12. The baffling materials are, for example, plugged alumina tubes to force the gas stream along the walls of the reactor to aid in cooling. Thus, the baffling and steel shot form a cooling zone in a reducing environment.

Figure 3:
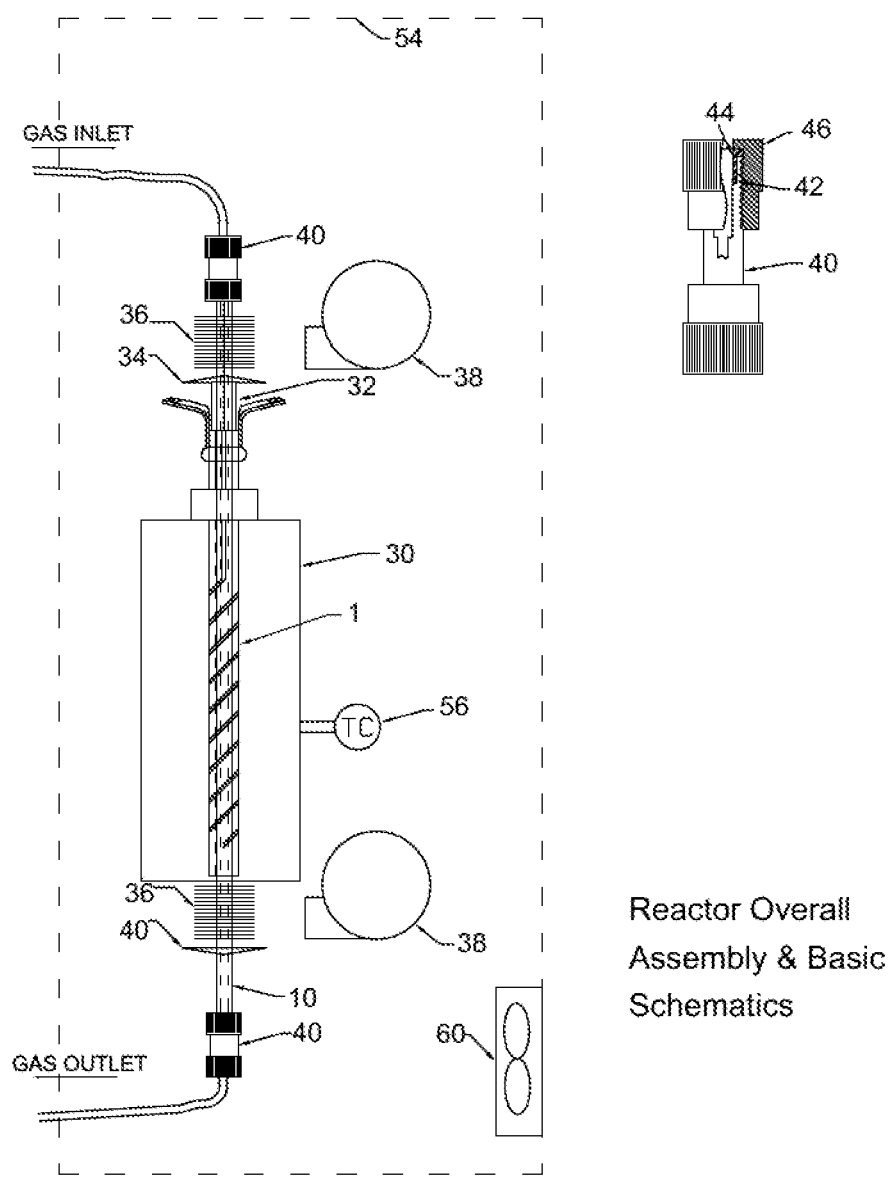
FIG. 3 depicts an overall reactor assembly of the embodiment in FIG. 2.

The overall reactor assembly is shown in FIG. 3. The alumina reactor 10 from FIG. 2 is central to the configuration. The reactor is placed down the center portion of the silicon carbide heater 1 from FIG. 1. The heater is wrapped in high temperature insulation that is contained inside a metallic housing 30. An insulating spacer 32 is placed above the heater on the reactor inlet to electrically isolate the metallic radiation shield 34 from the heater. Above the shield is an expanded surface area material 36 with a fan 38 blowing cool air over it to stop heat from conducting down the length of the reactor and melting the inlet tubing connectors 40.

The connectors 40 use an O-ring 42 and a backing ring 44 with a seal tension gland 46 to seal the fitting to the reactor tube. These connectors allow for a transition to be made to other metallic or non-metallic tubing for incoming stream flows and for outgoing stream flows. On the outlet of the reactor, the arrangement is similar to the incoming end (less the heater electrode apparatus) with an expanded metal heat diffuser 36, fan 38 and radiation heat shield 34 to quench the reactor outlet gases and protect the end connector. The entire reactor assembly is housed in a secondary housing 54 with an elevated temperature of approximately 50-70° C. to maintain the mercury in a vapor form as it enters and leaves the reactor.

The reactor is fitted with a temperature measurement instrument such as a thermocouple 56 to control the reactor temperature between 600 and 900° C. using a digital control strategy with the power supplied to the reactor heater. The power is regulated through a transformer and turned on and off using a power relay. The relay coil is energized from a temperature control loop either from a stand-alone controller or from a control computer. Over current protection is supplied by fuses or circuit breakers on both the primary and secondary circuits and all other secondary circuits as well.

The fans operate continuously upon system power up through receipt of a start signal via a computer control system or hard-wired start switch. The external housing is heated with residual heat from the reactor. A thermostatically controlled fan 60 draws fresh ambient air into the housing to control the internal temperature.

Turning to system performance for the embodiment shown in FIG. 3, the gas flow rate through the reactor can range from 0.2 liter per minute to 1.4 liters per minute with better conversions seen at higher flow rates. With a baseline of 16.3 microgram/cubic meter the following data was obtained with the reactor (Table 1). The analyzer used required 2000 cc/min. As the flow reached the required flow, the apparent conversion increased. Even as such, conversion of 85.9% was demonstrated.

TABLE 1

| Concentration, Microgram/cubic meter | Flow rate, cc/min |
|---|---|
| 5 | 204 |
| 10 | 500 |
| 12.8 | 1250 |
| 14 | 1400 |

This 85.9% conversion rate can meet EPA testing requirements. Other reactor configurations may yield higher conversion rate data.

The system has been tested by a number of experiments to determine some of the limits of this reduction process. Iron was used as the test metal in the form of steel wool because it has a relatively high surface area, and is known not to form stable amalgams with mercury. It also was chosen because electrochemically active metals (e.g. iron, zinc, and nickel) will reduce oxidized compounds of less active metals (e.g. mercury, copper, silver) to their elemental form. However, a problem still exists in that reconversion back to non-elemental mercury may occur. Thus, the embodiments described herein combine heating, scrubbing, and cooling with a reducing environment. The galvanic reduction of mercuric chloride by iron can be summarized by: $HgCl_2+Fe^- \rightarrow FeCl_x+Hg^0$, where x=2 or 3.

A number of mercury compounds, namely mercuric chloride, mercurous chloride, mercuric oxide, and mercuric nitrate were reacted with iron under dry conditions and in aqueous solutions. The reduction of these mercury compounds to elemental mercury occurred under both conditions, but the presence of moisture accelerated the reaction.

Under dry conditions, elevated temperature is needed to speed up the reaction. The presence of chloride ions in solution accelerated the reduction. Moisture and chloride ions, in the form of hydrogen chloride, are plentiful within flue gas streams. Iron was observed to reduce mercury even when wetted with Aqua Regia (nitro-hydrochloric acid), an extremely oxidizing environment. The mercury remains in the elemental form as long as the iron metal persists. This scenario was tested because the $NO_2$, HCl, and moisture in flue gas streams can combine to form Aqua Regia on the iron surface. Additionally, sulfuric acid will also be present when flue gas moisture condensation occurs making the acid solution even more oxidizing. It was also possible to separate the generated metallic mercury from the iron more easily under wet than dry conditions. In an experiment, evolution of vaporous elemental mercury was observed in real-time by observing analyzer readings by exposing steel shot to a moving gas stream with droplets of water solution containing mercuric chloride.

Iron, used in the galvanic reduction of mercury compounds has also been evaluated as a "coarse" scrub for the removal of $NO_x$ and HCl. When these gases were passed through a tube packed with moist steel wool, reaction was observed to occur. Since these reactions yield fresh iron surfaces, mercury reduction would be further enhanced.

Another experiment was set up to measure mercury concentration in a gas stream that included elemental and ionic mercury but that had been passed over a bed of steel shot prior to entering the analyzer. The average of a series concentration readings over a two hour period was compared to a separate sample prepared per Method 29 and analyzed using CVAAS (Method 7470A). The results were within 25% and since they were actually higher than the reference method, reduction was probably complete (Table 2).

TABLE 2

Galvanic Reduction vs. Reference Method

| Technique Used (2 hr. average) | Mercury Concentration |
|---|---|
| Steel shot | 116 micrograms/cu. Meter |
| Reference method 7470A | 94 micrograms/cu. Meter |

The iron will be consumed with present moisture and acid gases by the following possible reactions:

$$2NO_2(g)+H_2O(l) \rightarrow HNO_3(aq)+HNO_2(aq) \quad \text{(i)}$$

$$HCl(g) \rightarrow HCl(aq) \quad \text{(i)}$$

Other portions will react with the metal, illustrated by iron, as follows:

$$2HNO_3(aq)+Fe(s) \rightarrow Fe(NO_3)_2(aq)+H_2(g) \quad \text{(i)}$$

$$2HCl(aq)+Fe(s) \rightarrow FeCl_2(aq)+H_2(g) \quad \text{(ii)}$$

Oxides on the metal surfaces will also consume the acid gases.

Even with the effectiveness of the steel shot material to reduce the mercury, it was desired to remove as much of the acid gas prior to the reaction with the shot to increase the life of the shot in the reactor. Acid gases can be removed using a dry calcareous sorbent such as marble chips. Some initial experiments suggested that the moist sample stream in conjunction with a calcareous sorbent is very effective in scrubbing the acid gases. This reaction as well as the decomposition of ionic and organic mercury is also produced using a high temperature furnace (600 to 900'C.) prior to the steel shot galvanic reduction cooling zone.

For mercury compounds existing in the vapor phase, increasing the temperature thermodynamically drives their decomposition. The decomposition of the major mercury compounds that may exist in flue gas or other gaseous streams in this temperature range are as follows:

$$2HgO \rightarrow 2Hg+O_2 \quad \text{(I)}$$

$$Hg_2Cl_2 \rightarrow Hg+HgCl_2 \quad \text{(ii)}$$

Since mercuric chloride only undergoes partial decomposition even at 1200° C., the preceding decomposition reactions will yield elemental mercury (Hg) and mercuric chloride (HgCl$_2$) in the temperature range indicated above. However, since the chloride ions are removed from the gas stream through the neutralization reaction with the calcareous material the reaction is shifted to more complete decomposition to elemental mercury. Subsequent reductions complete the conversion in the steel shot zone.

During normal cooling of such a gas stream, thermodynamic equilibria will again produce the various ionic forms of mercury, namely mercurous chloride, mercuric chloride, and mercury oxide. The cooling process is performed in the environment of ferrous materials or other less noble metal than mercury. This less noble environment maintains a reducing environment to maintain the converted mercury in that form. It also further converts any ionic mercury through the reactions described previously. The metal also assists in cooling the gas stream more effectively due to the increased thermal conductivity of the media.

Once the ionic mercury compounds are thermally decomposed to elemental form, it is necessary to maintain them in that reduced state. The oxidative driving force increases as the temperature is lowered. Thus, to avoid re-oxidation, rapid quenching of the stream to a temperature sufficiently low for the reaction to be kinetically hindered is one approach to maintain the elemental form.

For further rapid temperature reduction, the pyrolyzer tube was designed to incorporate baffling in the cool down zone that would force the gas stream to the outermost section of the tube where it would have more contact with the exterior wall and increase its linear velocity as well. By incorporating an external heat sink and forced air fan for cooling the outer surface of the cool down region of the pyrolyzer tube, the cooling rate of the gas sample could be maximized. In addition, it was recognized that the presence of a reducing component such as iron in the pyrolyzer could also assist in the maintenance of the elemental form of the mercury.

A test was conducted to establish that there was no loss of elemental mercury through the sample conditioning system. This was done by using only an elemental mercury vapor source. Samples were drawn from before the reactor and after to establish any loss effect. The samples were analyzed by means of a calibrated gold film based mercury analyzer. The results are shown in Table 3 below.

TABLE 3

Comparison of samples taken prior to and after the pyrolytic sample conditioner.

| Sample Before Conditioner | Sample After Conditioner |
|---|---|
| (both are in µg/scm) | |
| 47.4 | 44.6 |
| 47.1 | 47.6 |
| 47.8 | 47.0 |
| 46.4 | 45.9 |
| 43.7 | 45.8 |
| 48.1 | 45.5 |
| 45.8 | 48.7 |
| Mean: 46.6 | Mean: 46.4 |

The means are identical within the error of measurement indicating that there is no loss of mercury vapor within the system.

In view of the system embodiments and reactions described above, sample conditioning and emission monitoring method embodiments are further described below. The sample conditioning systems (SCS) described herein improve upon known systems in a novel way to produce a system capable of converting mercury oxides and halides to elemental form and preserving this form for a period long enough to be analyzed.

Figure 4:
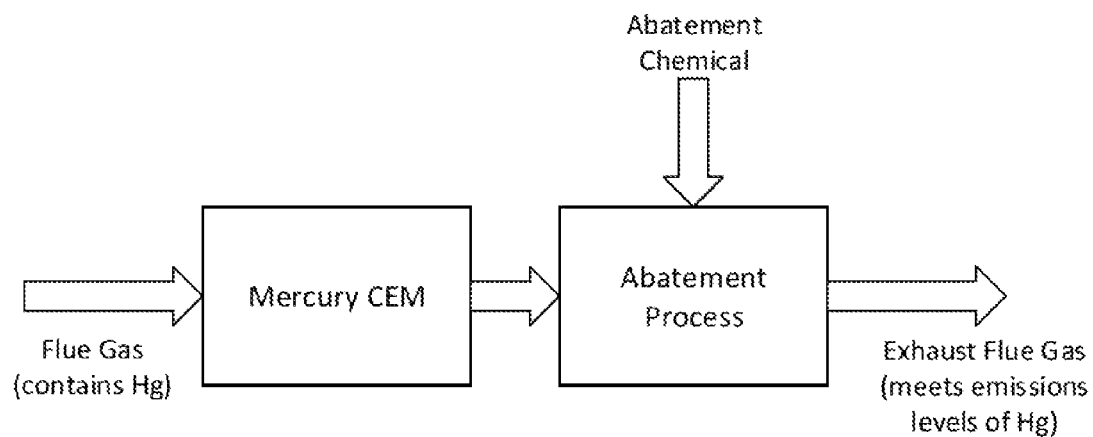
FIG. 4 shows the standard gas emissions mercury-abatement process of the prior art.

The purpose of a mercury SCS for emissions is to be coupled with an analyzer to allow for continuous emissions monitoring (CEM) of the gas stream. This CEM fits into overall processes as a measurement device able to determine the amount of abatement chemical needed to meet emissions requirements. The traditional method of using CEMs is diagrammed in FIG. 4. Using the traditional method is inefficient because more abatement chemical than necessary will likely be used to guarantee that the exhaust meets EPA requirements.

Figure 5:
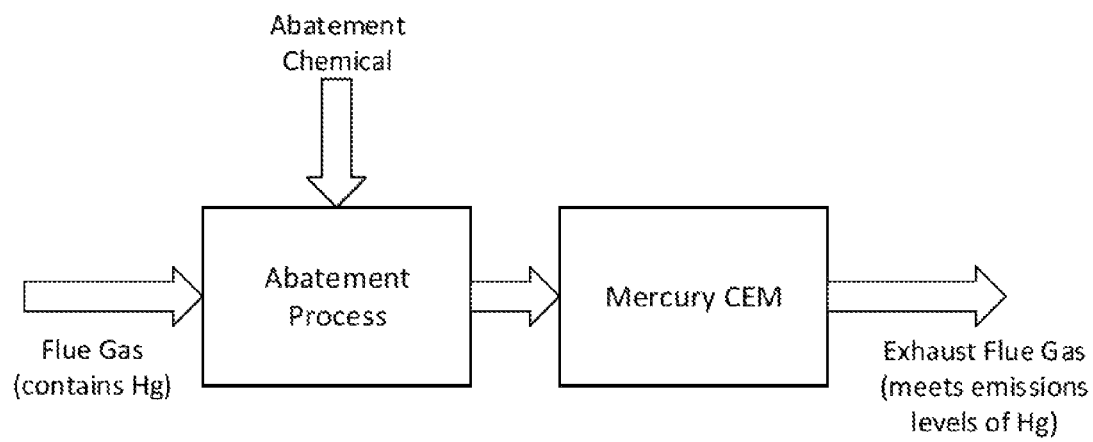
FIG. 5 illustrates a gas emissions mercury-abatement process embodiment of the invention.

A better method of treating flue gas is diagrammed FIG. 5. This method allows the CEM to read the mercury levels after the abatement process has happened, which absolutely verifies that the appropriate mercury levels have been reached. Moreover, greater control of the chemicals can then be exerted on the abatement process to save money while still meeting requirements.

Figure 6:
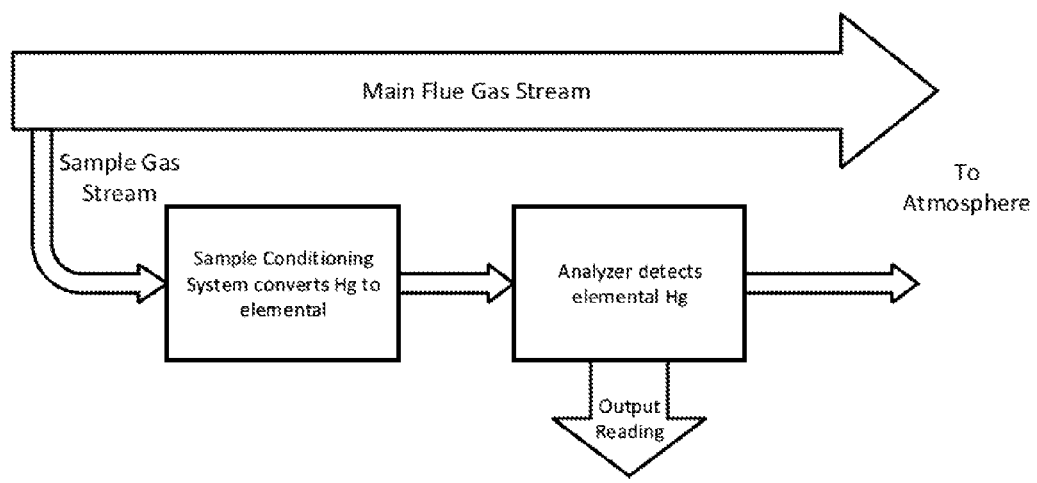
FIG. 6 illustrates a gas emissions mercury-monitoring process of the prior art.

All analyzers used in mercury CEMs are only capable of detecting the presence of elemental mercury. Since a flue gas stream will contain elemental, oxide, and halide forms of mercury, a sample conditioning system is necessary to convert these to their elemental state for analysis. A simple diagram of how mercury CEMs are put together is shown in FIG. 6.

The reason the FIG. 5 method has never been used in industry is because current mercury CEMs are incapable of reliably converting the mercury present after the abatement process to elemental form. The abatement process typically uses bromide to react with the mercury so that it can be absorbed. This creates a very stable molecule that is difficult to break back down to elemental form, as is necessary in a mercury CEM.

The improved methods and systems described herein achieve several important performance parameters. They allow the conversion to be done in some sort of pass-through system, conversion performance is very close to wet chemistry methods in terms of precision, system maintenance is minimal compared to wet chemistry methods, and mercury stays in elemental form throughout the sample conditioning and analysis/monitoring processes.

Figure 7:
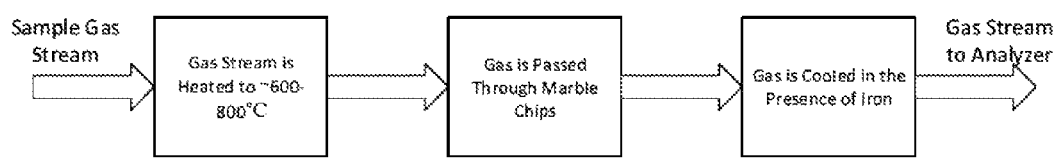
FIG. 7 depicts a gas emissions mercury-monitoring process according to the invention.

The systems described herein address every concern present in CEM technology. Additionally, they are the only systems that will allow a CEM to operate via the "ideal" FIG. 5 method. A basic flow chart of an improved system and method according to the invention is depicted in FIG. 7.

While the embodiments above have been described in the context of emissions conversion and monitoring, it is readily apparent that these systems and methods can be used to convert waste streams containing non-elemental forms of mercury into elemental form for further processing and disposal.

Various modifications are possible within the meaning and range of equivalence of the appended claims.

What is claimed is:

1. A sample conditioning system, comprising:
a reactor having a heater capable of heating said sample to at least 600° C., wherein said reactor is configured to include a calcareous sorbent zone and a galvanic reduction cooling zone formed by a wetted solid metal that is more chemically active or less noble than mercury, such that a heated sample flows through said calcareous sorbent and then is cooled in the galvanic reduction cooling zone by said wetted solid metal that is more chemically active or less noble than mercury.

2. The conditioning system of claim 1, wherein said calcareous sorbent comprises marble chips.

3. The conditioning system of claim 1, wherein said solid metal includes one or more of iron, zinc, and nickel.

4. The conditioning system of claim 1, wherein said metal is iron.

5. The conditioning system of claim 1, wherein said zone that includes solid metal that is more chemically active or less noble than mercury is adjacent to the calcareous sorbent zone.

6. The conditioning system of claim 1, additionally including a catalytic surface material integrated together with said calcareous sorbent in said calcareous sorbent zone.

7. The conditioning system of claim 6, wherein said catalytic surface material comprises quartz.

* * * * *